US012599681B2

(12) United States Patent
Williams et al.

(10) Patent No.: US 12,599,681 B2
(45) Date of Patent: Apr. 14, 2026

(54) FOAMABLE COMPOSITION FOR USE IN SURGICAL DIAGNOSTIC PROCEDURES

(71) Applicant: inx Medical, LLC, Chesterfield, MO (US)

(72) Inventors: Ken Williams, Chesterfield, MO (US); Chrysanthi Williams, Chesterfield, MO (US); Kurt Gampp, Chesterfield, MO (US); Jim Vermeersch, Chesterfield, MO (US)

(73) Assignee: inx Medical, LLC, Chesterfield, MO (US)

( * ) Notice: Subject to any disclaimer, the term of this patent is extended or adjusted under 35 U.S.C. 154(b) by 1150 days.

(21) Appl. No.: 17/596,802

(22) PCT Filed: Jun. 19, 2020

(86) PCT No.: PCT/US2020/038656
§ 371 (c)(1),
(2) Date: Dec. 17, 2021

(87) PCT Pub. No.: WO2020/257593
PCT Pub. Date: Dec. 24, 2020

(65) Prior Publication Data
US 2022/0296730 A1 Sep. 22, 2022

Related U.S. Application Data

(60) Provisional application No. 62/863,466, filed on Jun. 19, 2019.

(51) Int. Cl.
*A61K 49/00* (2006.01)
*A61B 17/11* (2006.01)

(52) U.S. Cl.
CPC .............. *A61K 49/00* (2013.01); *A61B 17/11* (2013.01)

(58) Field of Classification Search
CPC ..... A61K 49/00; A61B 17/11; A61L 26/0061; A61L 26/0085; A61L 2400/06; A61L 24/001; A61L 24/0036
See application file for complete search history.

(56) References Cited

U.S. PATENT DOCUMENTS

| | | | |
|---|---|---|---|
| 4,197,316 A | 4/1980 | Yu et al. | |
| 5,759,520 A | 6/1998 | Sachetto | |
| 7,033,526 B2 * | 4/2006 | Figiel ..................... | C09D 5/185 |
| | | | 252/607 |
| 8,216,159 B1 | 7/2012 | Leiboff | |
| 8,722,021 B2 | 5/2014 | Friedman et al. | |
| 11,452,481 B2 | 9/2022 | Geiger | |
| 2004/0018228 A1 | 1/2004 | Fischell et al. | |

| | | |
|---|---|---|
| 2004/0110643 A1 | 6/2004 | Zevallos |
| 2006/0216256 A1 | 9/2006 | Giniger et al. |
| 2006/0217637 A1 | 9/2006 | Leiboff et al. |
| 2008/0004566 A1 | 1/2008 | Sloan |
| 2008/0275403 A1 | 11/2008 | Maaskamp et al. |
| 2008/0312559 A1 | 12/2008 | Santilli et al. |
| 2011/0052665 A1 | 3/2011 | Hardy et al. |
| 2013/0138132 A1 | 5/2013 | Phee et al. |
| 2014/0081169 A1 | 3/2014 | Gerding et al. |
| 2014/0221732 A1 | 8/2014 | Dayton et al. |
| 2015/0017682 A1 | 1/2015 | Adam |
| 2015/0018597 A1 | 1/2015 | Fierens et al. |
| 2015/0045725 A1 | 2/2015 | Smith et al. |
| 2015/0351730 A1 | 12/2015 | Stokes et al. |
| 2017/0172877 A1 | 6/2017 | Buge et al. |
| 2018/0221633 A1 | 8/2018 | Brister et al. |
| 2019/0192433 A1 | 6/2019 | Buge et al. |

FOREIGN PATENT DOCUMENTS

| | | | |
|---|---|---|---|
| JP | 6562587 B1 * | 8/2019 | |
| WO | 1999/16454 A1 | 4/1999 | |
| WO | 2008051925 A2 | 5/2008 | |
| WO | 2014007821 A1 | 1/2014 | |
| WO | 2016022816 A1 | 2/2016 | |
| WO | 2016022973 A1 | 2/2016 | |

OTHER PUBLICATIONS

ThermoFisher Scientific, Safety Data Sheet, Revision No. 4, pp. 1-7. (Year: 2024).*
Vanderbilt Minerals, LLC, "Rheology Control Additives", Vanderbilt Minerals Report, No. 920 (year not provided).
https://cookingissues.com/primers/hydrocolloids-primer/ (year is not provided).
Cho, Hyun-Moon, Whachun Yoo, and Byoungseung Yoo. "Effect of NaCl Addition on rheological behaviors of commercial gum-based food thickener used for dysphagia diets." Preventive nutrition and food science 20.2 (2015): 137.
Seright, R. S., and B. J. Henrici. "Xanthan stability at elevated temperatures." SPE Reservoir Engineering 5.01 (1990): 52-60.
Ghannam, Mamdouh, Abu-Jdauil, Basim, and Esmail, Nabil. " Flow Behavior Comparison of Xanthan and Alcoflood Polymers Aqueous Solutions." American Journal of Oil and Chemical Technologies, vol. 1, Issue 2 (Mar. 2013): 1-11.
Vanderbilt Minerals, LLC, "Vanzan Xanthan Gum", (2018).

* cited by examiner

*Primary Examiner* — D. L. Jones
(74) *Attorney, Agent, or Firm* — Husch Blackwell LLP

(57) ABSTRACT

Provided herein are foamable compositions comprising (1) a base, in aqueous suspension, (2) a viscosity modifier component, and (3) a surfactant component. In preferred embodiments, the foamable composition may further comprise a salt. Additional components that may optionally be present in the formable composition include sugars and sugar alcohols, colorants, antioxidants, preservatives, and other excipients generally known to those skilled in the art. Also provided herein are kits for producing a gaseous foam. Also provided herein are methods for detecting the presence of leaks or defects in anatomical tissue or organ.

19 Claims, 2 Drawing Sheets

FOAMABLE COMPOSITION FOR USE IN SURGICAL DIAGNOSTIC PROCEDURES

CROSS REFERENCE TO RELATED APPLICATIONS

This application is a U.S. National Phase Application of International Application No. PCT/US2020/038656 filed on Jun. 19, 2020, which claims the benefit of priority from U.S. Patent Application No. 62/863,466, filed on Jun. 19, 2019.

BACKGROUND

The creation of an anastomosis is common in general surgery, colorectal surgery, urology, gynecology, and surgical oncology procedures. Unfortunately, leaks from an anastomosis are one of the most devastating complications that can occur after surgery. While reliable methods to test an anastomosis of the descending colon or rectum on the left side are well known, there are few reliable methods for testing an anastomosis of the small bowel and/or ascending and transverse colon on the right side.

A recent advance in the art involves using a liquid/gas foam to detect leaks in an anastomosis. WO/2017/189900 to Geiger describes a method comprising inserting an outlet of a delivery device into a lumen of an anastomosis of a bowel, delivering a sufficient amount of an acid and a sufficient amount of a base to the bowel, producing a gaseous foam when the acid and base react to distend the bowel, showing any area needing repair if the foam exits through defects in the anastomosis, and retracting the outlet of the delivery device from the lumen of the anastomosis.

For this surgical technique to be effective, the delivery device must create a sufficient volume of foam for the surgeon to detect and, if necessary, repair any leaks in the anastomosis. The foam should also be stable enough to last until any repairs to the anastomosis have been completed.

The use of the foam in a surgical context places many additional constraints on the formulation. Because the foam must only contain ingredients that are generally recognized as safe and approved by the Food and Drug Administration for use in surgical procedures, many excipients known to those skilled in the art will not be suitable. All components of the foam must be biocompatible, non-cytotoxic, non-genotoxic, non-carcinogenic, and must not exhibit any adverse effects on wound healing. The foamable composition must also be sterilizable to ensure the safety of the patient.

Additionally, the foamable composition, along with any other reagents (e.g., an activator composition) must be homogeneous suspensions or solutions that are easily shaken by hand to become uniform (if needed at all). Because surgical procedures are time sensitive, suitable compositions must not require extensive mixing by the physician or the surgical team, and in particular must be ready for use after hand mixing of no longer than about 15 seconds. Furthermore, to be useful in the surgical techniques described above, the foamable composition and reagents must be able to be aspirated by syringes and needles no larger than 16 gauge. The foamable composition and reagents must remain stable as homogeneous or uniform suspensions for at least 30 minutes, as they may be loaded into the syringes by the surgical team ahead of time before the surgeon is ready to use them. The foamable composition and reagents must exhibit sufficient shelf stability; they must remain stable and fully functional throughout their expected shelf life storage (at least 1-3 years) without the development of any harmful degradation products or other by-products and without any significant discoloration.

The surgical environment provides additional constraints relevant to the gaseous foam produced by the composition. The foam must be at or near physiologic pH for the intended tissue/organ application (e.g., from 6-7 pH for procedures involving the bowel). The foam must have a color that provides sufficient contrast with the intended tissue/organ application. It is also desirable that the foam development kinetics are as linear as possible—slow enough that surgeons have time to respond if the tissue/organ over-pressurizes, but also fast enough to be suitable for the time sensitive surgical environment.

Ideally, the foam quality and volume should remain near constant over the duration of its use during the procedure (e.g., 5 minutes) to allow the surgeon time for digital manipulation of the anastomosis and surrounding tissue for leak detection. The foam toughness should be high enough that foam can escape through small defects in the organ/tissue without collapsing. And the foam pressure should be high enough for leak detection, but also low enough that it does not distend the target tissue/organ. Finally, the foam should dissipate after a period of time and not provide any complications (e.g., when used to detect leaks in an anastomosis, it should not obstruct resuming bowel motility).

Furthermore, an ideal foamable composition would use a sufficiently low volume of liquid (e.g., less than 20 mL) to allow single-handed injection by the surgeon, while still producing a sufficient volume of foam to enable leak detection.

Accordingly, there exists a need in the industry to develop an aqueous suspension of a base such as sodium bicarbonate that is storage stable, biologically acceptable, and produces a more voluminous and longer lasting foam than formulations currently known in the art.

SUMMARY

Provided herein is a foamable composition comprising, for example, a base selected from the group consisting of sodium bicarbonate and potassium bicarbonate, wherein at least a portion of the base is present as an aqueous suspension; a pseudoplastic viscosity modifier having a shear yield stress no greater than about 3.5 Pa and a stationary yield stress no less than about 0.1 Pa; and a surfactant component comprising at least one nonionic surfactant.

Also provided herein is a foamable composition comprising, for example, sodium bicarbonate in a concentration of at least about 100 mg/mL, wherein at least a portion of the sodium bicarbonate is present as an aqueous suspension; a viscosity modifier comprising xanthan gum; and a surfactant component comprising at least one polysorbate derived from polyethoxylated sorbitan and oleic acid; wherein the mass ratio of the surfactant component to the viscosity modifier is from about 10:1 to about 50:1.

Also provided herein is a kit for creating a gaseous foam, the kit comprising, for example, a foamable composition as described herein; and an activator composition comprising an acid component.

Also provided herein is a method for testing the integrity of a cavity within an anatomical organ or tissue, the method comprising, for example, delivering into the cavity a foamable composition as described herein; delivering into the cavity an activator composition comprising an acid component; and contacting the foamable composition with the activator composition within the cavity, thereby creating a gaseous foam within the cavity.

Also provided herein is a method for testing the integrity of a cavity within an anatomical organ or tissue, the method comprising providing a foamable composition as described herein; providing an activator composition comprising an acid component; contacting the foamable composition with the activator composition thereby creating a gaseous foam; and delivering the gaseous foam to the cavity.

These and other aspects of the present disclosure are described in further detail below.

DETAILED DESCRIPTION

Figure 1:
FIG. 1 illustrates the effect of salt addition on the storage stability of the aqueous suspension; the two suspensions on the left of the image (without salt) began to show phase separation while the two suspensions on the right (including salt) remained stable.

Provided herein are foamable compositions that are useful, for example, in methods for detecting the presence of leaks or defects in anatomical tissue. Advantageously, the compositions described herein are capable of producing a greater volume of foam than compositions previously known in the art. In some embodiments, the foam has been particularly long-lasting, making it particularly useful in connection with the surgical methods described herein. The compositions have also been observed to be storage stable, and in preferred embodiments will only contain ingredients that are generally recognized as safe and approved by the Food and Drug Administration for use in surgical procedures.

The foamable compositions described herein will produce a gaseous foam upon contact with an activator composition. As used herein, the term "activator composition" may refer to an aqueous composition comprising an acid. For example, when a foamable composition comprising sodium bicarbonate in aqueous suspension is contacted with an activator composition comprising citric acid, the resulting generation of sodium citrate, water, and carbon dioxide will produce a gaseous foam.

Foamable Composition

A foamable composition as provided herein may comprise (1) a base such as sodium bicarbonate, in aqueous suspension, (2) a viscosity modifier component, and (3) a surfactant component. In preferred embodiments, the foamable composition may further comprise a salt. Additional components that may optionally be present in the foamable composition include sugar, colorants, antioxidants, preservatives, and other excipients generally known to those skilled in the art.
Base The foamable composition is preferably in the form of an aqueous suspension comprising a base. Preferably, the foamable composition comprises a base that is biologically acceptable and approved for use in surgical procedures. Non-limiting examples of bases include, for example, sodium bicarbonate and potassium bicarbonate. Sodium bicarbonate is the preferred base for the formulation.

It is desirable to include the base in an amount that maximizes the volume of foam produced per milliliter of solution, which in turn minimizes the amount of formulation that must be injected into the patient during a surgical procedure. On the other hand, the concentration of the base should not be so high that it adversely impacts the viscosity of the formulation and makes it difficult to inject using a syringe. The base will preferably be present in a concentration greater than its solubility limit in water. For example, the foamable composition may comprise the base in a concentration of at least about 100 mg/mL, at least about 200 mg/mL, at least about 300 mg/mL, at least about 400 mg/mL, at least about 500 mg/mL, or at least about 550 mg/mL. For example, the foamable composition may comprise the base in a concentration of from about 100 mg/mL to about 700 mg/mL, from about 200 mg/mL to about 700 mg/mL, from about 300 mg/mL to about 700 mg/mL, or from about 400 mg/mL to about 700 mg/mL.
Viscosity Modifier The foamable composition may further comprise one or more viscosity modifiers. Preferably, the composition comprises a pseudoplastic viscosity modifier. Without being bound to a particular theory, it is believed that the use of a pseudoplastic viscosity modifier, and in particular a viscosity modifier having a shear thinning rheology, will better prevent settling of the suspended sodium bicarbonate under the force of gravity.

The viscosity modifier preferably has a static yield stress of no greater than about 3.5 Pa. For example, the viscosity modifier may have a shear yield stress of no greater than about 2.5 Pa, no greater than about 3.0 Pa, or no greater than about 3.5 Pa.

The viscosity modifier preferably has a static yield stress of at least about 0.1 Pa. For example, the viscosity modifier may have a stationary yield stress of at least about 0.08 Pa, at least about 0.10 Pa, or at least about 0.15 Pa.

Non-limiting examples of viscosity modifiers include gums, polysaccharides, and polyacrylic acids. A particularly preferred viscosity modifier is xanthan gum. Xanthan gum is a pseudoplastic viscosity modifier having a relatively high static yield stress, and in the foamable compositions provided herein, relatively low concentrations of xanthan gum (e.g., 0.1-0.5 weight percent) are effective in stabilizing the sodium bicarbonate suspension.

In some embodiments, the foamable composition may comprise the viscosity modifier in a concentration of from about 0.001 g/mL (mL of total suspension) to about 0.01 g/mL. For example, the foamable composition may comprise the viscosity modifier in a concentration of from about 0.001 g/mL to about 0.003 g/mL, from about 0.003 g/mL to about 0.005 g/mL, or from about 0.005 g/mL to about 0.007 g/mL.

In preferred embodiments, the mass ratio of the surfactant component to the viscosity modifier is greater than about 10:1, greater than about 15:1, or greater than about 20:1. For example, the mass ratio of the surfactant component to the viscosity modifier may be from about 10:1 to about 100:1, from about 10:1 to about 50:1, from about 15:1 to about 50:1, or from about 20:1 to about 50:1. These ranges are particularly preferred when the viscosity modifier comprises xanthan gum and the surfactant component comprises a polysorbate (e.g., polysorbate 80).
Surfactant Component The foamable composition may further comprise a surfactant component comprising one or more surfactants. For example, the composition may comprise one or more anionic or nonionic surfactants. Preferably, the composition comprises a nonionic surfactant. It has been found that the presence of a surfactant decreases the surface tension of the formulation and stabilizes the foam through a variety of mechanisms, resulting in a longer-lasting durable foam that is highly desirable for use in the surgical methods described herein.

Non-limiting examples of surfactants that may be incorporated into the foamable composition include polyols and polysorbates. Examples of polyols that may be incorporated into the composition include, but are not limited to, glycerol and sorbitol. Preferred polysorbates include those derived from polyethoxylated sorbitan and oleic acid. For example, the foamable composition may comprise a surfactant selected from the group consisting of polysorbate 60 and polysorbate 80.

In some embodiments, the foamable composition may comprise the surfactant component in a concentration of from about 0.1% by weight to about 5% by weight of the composition as a whole. For example, the foamable composition may comprise the surfactant component in a concentration of from about 0.1% to about 2%, from about 0.1% to about 1%, or from about 0.2% to about 1% by weight of the composition as a whole.

Ionic Strength Modifier

The foamable composition may further comprise one or more ionic strength modifiers. The ionic strength modifier may comprise, for example, a salt. Non-limiting examples of salts include sodium chloride and potassium chloride; other food-safe mineral salts are known to those skilled in the art. For example, the foamable composition may comprise sodium chloride (table salt). Without being bound to a particular theory, it is believed that salt will modify ionic solution strength and coordinate with the viscosity modifier (e.g., xanthan gum) to modify rheological behavior and provide tunable static yield stress.

In some embodiments, the foamable composition may comprise the salt in a concentration of from about 0.1 weight percent to about 10 weight percent. For example, the foamable composition may comprise the salt in a concentration of from about 1% to about 10%, from about 2% to about 8%, or from about 3% to about 7% by weight of the composition as a whole.

Dispersing Agent

The foamable composition may further comprise a dispersing agent. For example, the dispersing agent may comprise a sugar or a sugar alcohol. Non-limiting examples of sugars that may be incorporated into the composition include sucrose, maltose, lactose, glucose, fructose, and galactose. Non-limiting examples of sugar alcohols that may be incorporated into the composition include sorbitol, mannitol, xylitol, isomalt, and hydrogenated starch hydrolysates. For example, the foamable composition may comprise sucrose (table sugar). Without being bound to a particular theory, it is believed that the sugar will coordinate with the viscosity modifier (e.g., xanthan gum) and reduce the amount of bonding between the viscosity modifier and water. The presence of a sugar will thus prevent clumping and promote an evenly dispersed suspension during manufacture of the foamable composition.

In some embodiments, the foamable composition may comprise sugar in a concentration of from about 0.1% to about 10% by weight of the composition. For example, the foamable composition may comprise sugar in a concentration of from about 0.5% to about 8% by weight, from about 1% to about 5% by weight, or from about 1% to about 3% by weight of the composition.

Colorant

The foamable composition may further comprise a colorant (e.g., a dye). The presence of a colorant facilitates the easy visual identification of the foam produced by the foamable composition. For example, when the foam is used in connection with a method for detecting defects in an anatomical organ or tissue as described herein, the presence of a colorant may make it easier to visually identify any defect through which the foam has escaped by providing contrast between the foam color and the tissue or organ.

Additional Components

The foamable composition may further comprise one or more pharmaceutically acceptable excipients. Suitable excipients are generally known to those skilled in the art. Non-limiting examples of suitable excipients include antioxidants, preservatives, and buffering agents. For example, the foamable composition may further comprise an antioxidant. Non-limiting examples of preferred antioxidants include butylated hydroxytoluene (BHT) and ethylenediaminetetraacetic acid (EDTA). Other non-limiting examples of additives that may be used include antibiotics such as erythromycin, neomycin, and metronidazole, antioxidants such as vitamin E, vitamin A, and vitamin C, probiotics such as lactobacillus, and acidophilus, prebiotics such as chicory root, burdock root, promotility agents such as metoclopramide and bethanechol, laxatives such as polyethylene glycol and magnesium citrate, growth factors and polypeptides such as vascular endothelial growth factor and teduglutide, fiber, medium-chain fatty acids, glutamine, and amino acids such as alanine, leucine and isoleucine.

Activator Composition

As noted above, the foamable compositions described herein will produce a gaseous foam upon contact with an activator composition. Preferably, the activator composition is an aqueous composition comprising an acid component. Non-limiting examples of acids that may be present in the activator composition include acetic acid, ascorbic acid, citric acid, folic acid, fumaric acid, lactic acid, malic acid, and tartaric acid. In preferred embodiments, the activator composition comprises citric acid.

The activator composition may comprise the acid component in a concentration of at least about 100 mg/mL, at least about 200 mg/mL, at least about 300 mg/mL, at least about 400 mg/mL, or at least about 450 mg/mL.

Delivery Kits

Also provided herein are kits for creating a gaseous foam. The kit may, for example, comprise a foamable composition and an activator composition as described herein. In preferred embodiments, the kit comprises the foamable composition and the activator composition in predetermined amounts such that the ratio of base (in the activator composition) to the acid component (in the activator composition) is stoichiometrically equivalent. For example, the molar ratio of the base to the acid component can be from about 1:10 to about 10:1, from about 1:5 to about 5:1, from about 1:4 to about 4:1, from about 1:3 to about 3:1, from about 1:2 to about 2:1, or about 1:1.

In some embodiments, the kit may comprise a dehydrated or lyophilized foamable composition, for example in the form of a powder. In such embodiments, the kit may comprise instructions for dispersing the powder in water to create a foamable composition in the form of an aqueous suspension as described herein.

In some embodiments, the kit may comprise a frozen foamable composition. In such embodiments, the kit may comprise instructions for thawing the solutions to create a foamable composition in the form of an aqueous suspension as described herein.

Also provided herein is a kit for testing the integrity of a cavity within an anatomical organ or tissue. In addition to a foamable composition and an activator composition as described herein, the kit may further comprise a device suitable for delivering the foamable composition and the activator composition to the cavity, where the compositions may subsequently mix and produce a foam. One such device is described, for example, in WO/2017/189900, the entire contents of which are incorporated herein by reference.

Methods of Detecting Leaks or Defects in Anatomical Tissue

Provided herein are methods for detecting the presence of leaks or defects in anatomical tissue.

For example, provided herein are methods for testing the integrity of a cavity within an anatomical organ or tissue. For example, the method can comprise producing a gaseous foam within the cavity. The method can further comprise identifying any defects through which the gaseous foam exits the anatomical organ or tissue.

The foam may be produced within the cavity using any means known in the art. For example, the method may comprise delivering a foamable composition and an activator composition to the interior of the cavity, where the compositions are allowed to mix and produce a gaseous foam as described herein. Alternatively, the method may comprise contacting a foamable composition and an activator composition to produce a gaseous foam, followed by delivering the gaseous foam to a cavity. In a preferred embodiment, the gaseous foam is delivered to the interior of the cavity using a device as described in WO/2017/189900.

The methods described herein can be used to detect leaks or test the integrity or repair of any cavity, interior space, or lumen within any anatomical tissue or organ, including but not limited to those of the gastrointestinal tract (e.g., stomach, small intestine, large intestine, colon, rectum, etc.), urinary tract (e.g., bladder), or vagina.

For example, the methods described herein may be used to test the integrity of a tissue or organ of the gastrointestinal tract, including but not limited to the stomach, small intestine, large intestine, colon, and rectum. The methods described herein may be particularly useful for testing the integrity of a bowel, and in particular the integrity of an anastomosis of a bowel.

The acid and the base may be selected as described above, and are preferably delivered to the cavity in a molar ratio as described above.

The methods can further comprise delivering a colorant to the cavity. Among other advantages, the presence of a colorant facilitates the easy identification of the gaseous foam produced by the mixture of the acid and base, for example by producing a colored gaseous foam. This in turn facilitates the easy identification of any defects in the anatomical organ or tissue, which will be indicated by the presence of a colored gaseous foam escaping through such a defect. The colorant may be selected as described above.

The methods may further comprise repairing a defect in the anatomical organ or tissue, if necessary. For example, where the method is used to test for leaks in an anastomosis, the method may further comprise repairing the anastomosis if a defect is identified wherein the gaseous foam exits the anastomosis.

Other objects and features will be in part apparent and in part pointed out hereinafter.

EXAMPLES

The following non-limiting examples are provided to further illustrate the present disclosure.

Example 1: Components

The components described below were used in each of the following examples, unless otherwise indicated.

Aqueous solutions of citric acid solution were prepared in 100 mL beakers using a citric acid concentration of 445 mg/mL. Aqueous suspensions of sodium bicarbonate were prepared in 50 or 100 mL beakers using a sodium bicarbonate concentration of 583 mg/mL. Polysorbate 80 was provided as TWEEN 80, available from Sigma-Aldrich.

After the addition of additives to the sodium bicarbonate composition (as described in greater detail below), the citric acid composition and sodium bicarbonate composition were mixed using a mechanical stirrer and combined in a 250 mL graduated cylinder to measure the total volume of foam created.

Example 2: Control Experiments Using Sodium Carbonate Below the Solubility Limit A citric acid composition was prepared as described in Example 1 above, except that the citric acid concentration was set at 69 mg/mL. A sodium bicarbonate composition was prepared as described in Example 1 above, except that the sodium bicarbonate concentration was set at 90 mg/mL. The two liquids were simultaneously injected into graduated cylinder at a 10 and 20 mL volume each. In all cases, some bubbles were created, but the mixture failed to produce any appreciable volume of foam.

Example 3: Sodium Bicarbonate With Glycerol or Sorbitol

Sodium bicarbonate and citric acid compositions were prepared as described in Example 1. Injection of either 3 mL+3 mL or 5 mL+5 mL gave same resultant 20-30 mL of foam volume. Various dilutions of the sodium bicarbonate suspensions with water failed to improve the foam volumes generated. It was hypothesized that sorbitol alone did not provide appropriate viscosity modifier needed to properly suspend the sodium bicarbonate, nor did it provide proper surface tension modification.

Example 4: Sodium Bicarbonate With Lecithin

A sodium bicarbonate suspension was prepared using 5.84 grams of sodium bicarbonate, 1.27 grams of lecithin, and 5.94 grams water. Vials of the sodium bicarbonate+ lecithin composition were stored at room temperature for approximately 4 weeks. Upon examination, the compositions were highly viscous and not like the freshly prepared material.

Some discoloration had occurred (tannish) indicative of some type of aging effect. It was very difficult to pull suspension from the vial with a 16 gauge needle. Mixing 3 mL of the sodium bicarbonate composition with 3 mL of a citric acid composition in a graduated cylinder resulted in the production of 110 mL of foam. Aging the material at room temperature for 1 week resulted in significantly less foam generated than with freshly prepared material.

Example 5: Sodium Bicarbonate With Lecithin and Polysorbate 80

A sodium bicarbonate suspension was prepared using 5.84 grams of sodium bicarbonate, 0.87 grams of lecithin, 136.6 milligrams of polysorbate 80, and 5.99 grams water. Mixing 4 mL of the sodium bicarbonate composition with 4 mL of a citric acid composition in a graduated cylinder resulted in the production of 210 mL of a stable homogeneous foam. The test was repeated with both lower and higher concentrations of polysorbate 80, each of which produced less foam than the formulation identified above.

Example 6: Sodium Bicarbonate With Xanthan Gum and Polysorbate 80

A sodium bicarbonate suspension was prepared as described in Example 5, except using xanthan gum instead of lecithin. Loadings of less than 0.01 g/mL of xanthan gum resulted in the formation of a thick sodium bicarbonate suspension which produced visibly larger bubbles than the lecithin mixture described in Example 6. Mixing 4 mL of the sodium bicarbonate composition with 4 mL of a citric acid composition in a graduated cylinder resulted in the production of between 90 and 170 mL of foam.

Titration of the xanthan gum suspension with various loadings of polysorbate 80 revealed an optimum loading of ~1-2.5 g of polysorbate 80 per 18 grams of water (~2-3 weight percent of P80). Resulting foam volumes were 90 to 210 mL. It was observed that 210 mL was the highest repeatable volume achieved using a combination of xanthan gum and polysorbate 80.

Example 7: Sodium Bicarbonate With Xanthan Gum, Polysorbate 80, and Table Salt It was hypothesized that controlling the ionic strength of the xanthan gum-based emulsion could improve the rheological properties of the emulsion. This hypothesis was tested by varying the concentration of NaCl in the xanthan gum+polysorbate 80 matrix.

A first sodium bicarbonate suspension was prepared by adding 5 weight percent of NaCl, ~0.3 weight percent of xanthan gum, and 5 weight percent of polysorbate 80. Upon mixing 4 mL of the sodium bicarbonate composition with 4 mL of a citric acid composition, approximately 250 mL of foam was produced. Addition of more xanthan gum or polysorbate 80 reduced the foam volume created.

A second sodium bicarbonate suspension was prepared by adding 2.5 weight percent of NaCl, ~0.2 weight percent of xanthan gum, and 3 weight percent of polysorbate 80. Upon mixing 4 mL of the sodium bicarbonate composition with 4 mL of a citric acid composition, between 290-300 mL of foam was repeatably produced (n=3).

One trend observed from the experiments with xanthan gum and polysorbate 80 was that lower apparent viscosity resulted in the production of appreciably more foam. Hence, it was hypothesized that an optimal formulation would comprise enough xanthan gum to stabilize sodium bicarbonate suspension, but not too much to markedly reduce foamability. Polysorbate 80 was hypothesized to favorably improve the surface tension of the suspension, critical micelle concentration, liquid drainage, and increase foam volumes.

FIG. 1 illustrates the effect of salt addition on the storage stability of the aqueous suspension. As shown in FIG. 1, the two suspensions on the left of the image (without salt) began to show phase separation while the two suspensions on the right (including salt) remained stable. Without being bound to a particular theory, it has been observed that salt increases the static yield stress without markedly changing the viscosity of the composition under shear.

Figure 2:
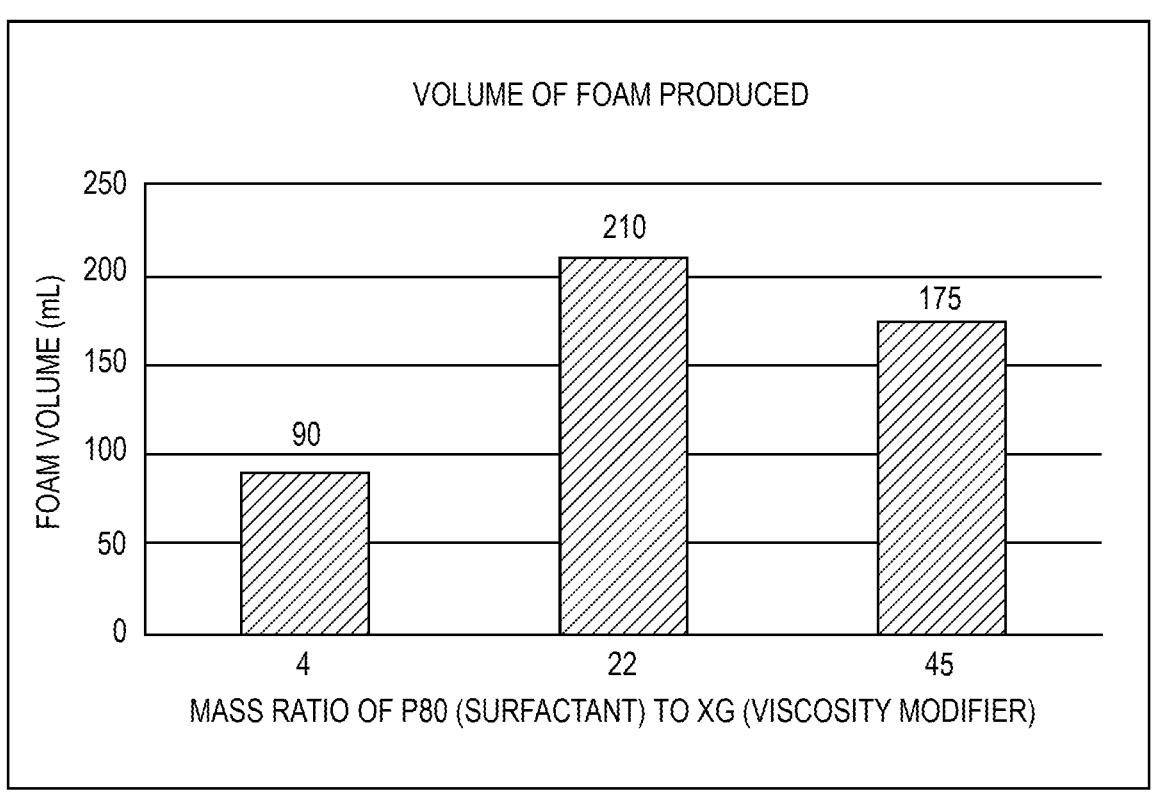
FIG. 2 illustrates the effect of the mass ratio of surfactant (polysorbate 80) to viscosity modifier (xanthan gum) on the total value of foam produced at 2 minutes after combining 4 mL of the sodium bicarbonate composition with 4 mL of a citric acid composition.

FIG. 2 illustrates the effect of the mass ratio of surfactant (polysorbate 80) to viscosity modifier (xanthan gum) on the total value of foam produced at 2 minutes after combining 4 mL of the sodium bicarbonate composition with 4 mL of a citric acid composition. As shown in FIG. 2, an optimal formulation comprises enough xanthan gum to stabilize the sodium bicarbonate suspension, but not too much to markedly reduce foamability.

Example 8: Aging Studies With Formulations From Examples 6 and 8

The sodium bicarbonate compositions prepared as described in Examples 6 and 8 (second composition) were aged 7 days at room temperature and tested again for foam generation. Both sodium bicarbonate suspensions were stirred vigorously with a lab spatula prior to testing. The lecithin+polysorbate 80 suspension from Example 6 produced significantly less foam volume after aging for 7 days (120 mL of foam for aged sample vs. 210 mL of foam for fresh sample). This phenomenon is comparable to the results from Example 5 with the 4-week-old aged vials.

In contrast, the sample from Example 8 had no measurable aging effects over 7 days. The foam volume generated after 7 days of aging was the same (~300 mL) as the freshly prepared sodium bicarbonate suspension. The aged suspension was further allowed to sit for 30 min undisturbed after mixing and then retested without any further mixing. Again, the generated foam volume was ~300 mL, indicating that the suspension remains stable for at least 30 minutes.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

In view of the above, it will be seen that several objects of the disclosure are achieved and other advantageous results attained.

As various changes could be made in the above products and methods without departing from the scope of the disclosure, it is intended that all matter contained in the above description shall be interpreted as illustrative and not in a limiting sense.

What is claimed is:

1. A foamable composition comprising:
   a base selected from the group consisting of sodium bicarbonate and potassium bicarbonate, wherein at least a portion of the base is present as an aqueous suspension;
   a pseudoplastic viscosity modifier selected from the group consisting of gums, polysaccharides, and polyacrylic acids, wherein the pseudoplastic viscosity modifier has a shear yield stress no greater than about 3.5 Pa and a stationary yield stress no less than about 0.1 Pa; and a surfactant component comprising at least one nonionic surfactant;

wherein the composition comprises the base in a concentration of at least about 100 mg/mL.

2. The composition of claim 1 wherein the composition comprises sodium bicarbonate in a concentration of at least about 200 mg/mL.

3. The composition of claim 1 wherein the viscosity modifier selected is a gum.

4. The composition of claim 3 wherein the viscosity modifier is xanthan gum.

5. The composition of claim 1 wherein the composition comprises at least one nonionic surfactant selected from the group consisting of polyols and polysorbates.

6. A foamable composition comprising:

sodium bicarbonate in a concentration of at least about 100 mg/mL, wherein at least a portion of the sodium bicarbonate is present as an aqueous suspension;

a viscosity modifier comprising xanthan gum; and a surfactant component comprising at least one polysorbate derived from polyethoxylated sorbitan and oleic acid;

wherein the mass ratio of the surfactant component to the viscosity modifier is from about 10:1 to about 50:1.

7. The composition of claim 6 wherein the composition comprises at least one polysorbate selected from the group consisting of polysorbate 60 and polysorbate 80.

8. The composition of claim 7 wherein the composition comprises polysorbate 80.

9. The composition of claim 6 wherein the composition comprises the viscosity modifier in a concentration of from about 0.001 g/mL to about 0.01 g/mL.

10. The composition of claim 6 comprising the surfactant component in a concentration of from about 0.1% to about 5% by weight of the composition.

11. The composition of claim 6 wherein the composition further comprises sodium chloride.

12. The composition of claim 6 wherein the composition further comprises a sugar selected from the group consisting of sucrose, maltose, lactose, glucose, fructose, and galactose.

13. The composition of claim 12 wherein the composition comprises the sugar in a concentration of from about 0.1% to about 10% by weight.

14. A kit for creating a gaseous foam, the kit comprising:

a foamable composition as set forth in claim 6; and an activator composition comprising an acid component selected from the group consisting of acetic acid, ascorbic acid citric acid, folic acid, fumaric acid, lactic acid, malic acid, and tartaric acid.

15. The kit of claim 14 wherein the molar ratio of the sodium bicarbonate in the foamable composition to the acid component in the activator composition is from about 1:10 to about 10:1.

16. A method for producing a gaseous foam, the method comprising:

providing a foamable composition as set forth claim 6;

providing an activator composition comprising an acid component selected from the group consisting of acetic acid, ascorbic acid, citric acid, folic acid, fumaric acid, lactic acid, malic acid, and tartaric acid; and contacting the foamable composition with the activator composition.

17. A method for testing the integrity of a cavity within an anatomical organ or tissue, the method comprising:

delivering into the cavity a foamable composition as set forth in claim 6;

delivering into the cavity an activator composition comprising an acid component selected from the group consisting of acetic acid, ascorbic acid, citric acid, folic acid, fumaric acid, lactic acid, malic acid, and tartaric acid; and contacting the foamable composition with the activator composition within the cavity, thereby creating a gaseous foam.

18. A method for testing the integrity of a cavity within an anatomical organ or tissue, the method comprising:

providing a foamable composition as set forth claim 6;

providing an activator composition comprising an acid component selected from the group consisting of acetic acid, ascorbic acid, citric acid, folic acid, fumaric acid, lactic acid, malic acid, and tartaric acid;

contacting the foamable composition with the activator composition thereby creating a gaseous foam; and delivering the gaseous foam to the cavity.

19. The composition of claim 6 wherein the composition comprises sodium bicarbonate in a concentration of at least about 200 mg/mL.

\* \* \* \* \*